US010684377B2

(12) United States Patent
Morimoto et al.

(10) Patent No.: US 10,684,377 B2
(45) Date of Patent: Jun. 16, 2020

(54) SCINTILLATOR, SCINTILLATOR ARRAY, RADIATION DETECTOR, AND RADIATION INSPECTION DEVICE

(71) Applicants: KABUSHIKI KAISHA TOSHIBA, Tokyo (JP); TOSHIBA MATERIALS CO., LTD., Yokohama-Shi (JP)

(72) Inventors: Kazumitsu Morimoto, Yokohama (JP); Yoshitaka Adachi, Yokohama (JP); Yukihiro Fukuta, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 118 days.

(21) Appl. No.: 15/963,137

(22) Filed: Apr. 26, 2018

(65) Prior Publication Data
US 2018/0252824 A1 Sep. 6, 2018

Related U.S. Application Data

(63) Continuation of application No. PCT/JP2016/082542, filed on Nov. 2, 2016.

(30) Foreign Application Priority Data

Nov. 2, 2015 (JP) ................... 2015-215683

(51) Int. Cl.
*G01T 1/202* (2006.01)
*A61B 6/03* (2006.01)
(Continued)

(52) U.S. Cl.
CPC .............. *G01T 1/2023* (2013.01); *A61B 6/03* (2013.01); *C09K 11/00* (2013.01);
(Continued)

(58) Field of Classification Search
CPC .... C04B 2235/3224; C04B 2235/5436; C04B 2235/446; G01T 1/2023
See application file for complete search history.

(56) References Cited

U.S. PATENT DOCUMENTS 5,296,163 A   3/1994  Leppert et al.
5,609,793 A   3/1997  Yokota et al.
(Continued)

FOREIGN PATENT DOCUMENTS

JP   H06-206769 A1   7/1994
JP   H07-188655 A1   7/1995
(Continued)

OTHER PUBLICATIONS

International Search Report and Written Opinion (Application No. PCT/JP2016/082542) dated Dec. 13, 2016.
(Continued)

*Primary Examiner* — Kenneth J Malkowski
(74) *Attorney, Agent, or Firm* — Burr & Brown, PLLC

(57) ABSTRACT

A scintillator comprises a sintered body having a volume of 1 mm³ or less. The sintered body includes a crystal region of a rare earth oxysulfide. The number of polycrystal bodies each having a different composition from that of the crystal region is 200 or less per a unit area of 100 μm×100 μm of a cross section of the sintered body.

9 Claims, 11 Drawing Sheets
(4 of 11 Drawing Sheet(s) Filed in Color)

(51) Int. Cl.
- *G21K 4/00* (2006.01)
- *G01N 23/04* (2018.01)
- *C09K 11/00* (2006.01)
- *G01T 1/20* (2006.01)
- *C09K 11/77* (2006.01)
- *G01N 23/046* (2018.01)

(52) U.S. Cl.
CPC ......... *C09K 11/7771* (2013.01); *G01N 23/04* (2013.01); *G01N 23/046* (2013.01); *G01T 1/20* (2013.01); *G01T 1/2002* (2013.01); *G01T 1/202* (2013.01); *G21K 4/00* (2013.01)

(56) References Cited

U.S. PATENT DOCUMENTS

| | | | | |
|---|---|---|---|---|
| 6,504,156 | B1* | 1/2003 | Takahara | C09K 11/7771 250/361 R |
| 2006/0145085 | A1* | 7/2006 | Fukuta | C04B 35/547 250/370.11 |
| 2008/0210885 | A1 | 9/2008 | Bolyasnikova et al. | |
| 2012/0145962 | A1* | 6/2012 | Fukuta | C09K 11/7774 252/301.4 R |
| 2013/0108008 | A1* | 5/2013 | Levene | G01T 1/2002 378/4 |
| 2015/0033541 | A1* | 2/2015 | Nitta | G01T 1/20 29/460 |

FOREIGN PATENT DOCUMENTS

| | | |
|---|---|---|
| JP | H07-252476 A1 | 10/1995 |
| JP | H09-202880 A1 | 8/1997 |
| JP | 2001-089762 A1 | 4/2001 |
| JP | 2004-101367 A1 | 4/2004 |
| JP | 2004-204053 A1 | 7/2004 |
| JP | 4959877 B2 | 6/2012 |
| JP | 2012-187137 A1 | 10/2012 |

OTHER PUBLICATIONS

Extended European Search Report (Application No. 16862111.8) dated Jun. 5, 2019.

* cited by examiner

US 10,684,377 B2

SCINTILLATOR, SCINTILLATOR ARRAY, RADIATION DETECTOR, AND RADIATION INSPECTION DEVICE

CROSS-REFERENCE TO RELATED APPLICATIONS

This application is a continuation of prior International Application No. PCT/JP2016/082542, filed on Nov. 2, 2016 which is based upon and claims the benefit of priority from Japanese Patent Application No. 2015-215683, filed on Nov. 2, 2015; the entire contents of all of which are incorporated herein by reference.

BACKGROUND OF THE INVENTION

1. Field of the Invention

Embodiments described herein generally relate to a scintillator, a scintillator array, a radiation detector, and a radiation inspection device.

2. Description of Related Art

Radiation inspection devices such as an X-ray CT (Computed Tomography: CT) device have been used for various fields including medical use, industrial use, or the like. For example, there is disclosed a multi-slice X-ray CT device provided with a scintillator array which has detection elements (photodiodes or the like) vertically and horizontally arranged in two dimensions. Employment of a multi-slice type makes it possible to superpose cross-sectional images, whereby three-dimensionally expressing the CT image is enabled. A radiation detector mounted on the radiation inspection device includes a plurality of detection elements arranged vertical and horizontal lines. Each of the plurality of detection elements is provided with a scintillator. In other words, one scintillator is provided in one detection element.

An X-ray incident on the scintillator is converted into visible light, and the visible light is converted into an electric signal by the detection element and output as an image. In recent years, in order to obtain high resolution, the detection element is downsized and a pitch between adjacent detection elements is reduced. Accompanying the above, a size of the scintillator is also reduced to 1 mm³ or less in volume.

As for a material of the scintillator, for example, a ceramic scintillator made of a gadolinium oxysulfide sintered body can be cited. A body color of the ceramic scintillator indicates certain chromaticity coordinates (x, y). The chromaticity coordinates are measured by using a color meter. A minimum measurement range of a general color meter is about 2 to 8 mm in diameter. A measurement area of the measurement range when a diameter is 2 to 8 mm, for example, is 3.14 to 50.24 mm². The chromaticity is regarded as appropriate even when a minute discoloration region of less than about 1 mm² in area exists in the above range. The discoloration region means a discoloration region existing in one ceramic scintillator.

In a case where the ceramic scintillator is small in size, influence on emission characteristics due to comparatively minute discoloration region becomes large when the minute discoloration region exists. That is, if the minute discoloration region is generated, an optical output at the time that the X-ray is converted into visible light is reduced. In particular, in the scintillator array having a plurality of ceramic scintillators arranged vertically and horizontally in two dimensions, when the optical output of the ceramic scintillator partly decreases, sensitivity variation of the scintillator array becomes large. The ceramic scintillator is manufactured by being cut out of an ingot being a large sintered body. When the minute discoloration region exists in the ingot, the optical output of each ceramic scintillator is reduced, resulting in sensitivity variation of the scintillator array.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

A scintillator comprises a sintered body having a volume of 1 mm³ or less. The sintered body includes a crystal region of a rare earth oxysulfide. The number of polycrystal bodies each having a different composition from that of the crystal region is 200 or less per a unit area of 100 μm×100 μm of a cross section of the sintered body.

A scintillator of an embodiment has a sintered body that has a volume of 1 mm³ or less and includes a crystal region of a rare earth oxysulfide. If a minute discoloration region exists inside the sintered body, influence on emission characteristics due to the comparatively minute discoloration region is large.

As a result of investigation and analysis of a cause of the discoloration region, the discoloration region has a region in which polycrystal bodies represented by a composition deviating from that of the rare earth oxysulfide gather (region which contains polycrystal bodies represented by the composition deviating from the composition of the crystal region of the rare earth oxysulfide) inside the rare earth oxysulfide sintered body such as gadolinium. Further, the region in which the polycrystal bodies gather is an impurity-containing region in which impurities exist. That is, the minute discoloration region is the region in which the polycrystal bodies represented by the composition deviating from that of the rare earth oxysulfide gather and, further, also the impurity-containing region.

Figure 1:
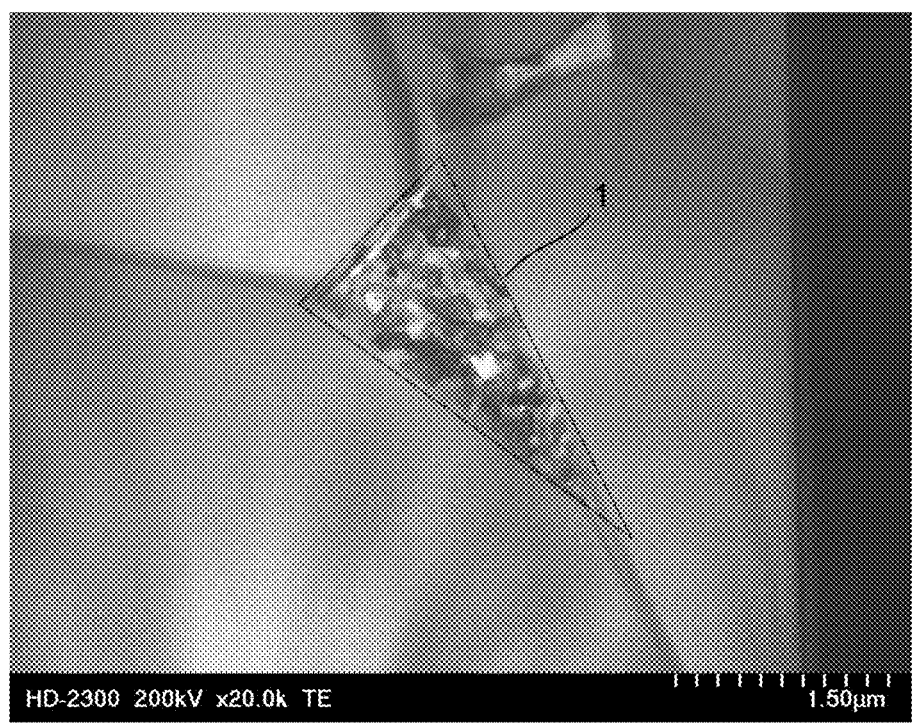
FIG. 1 is a view illustrating an observation image of a polycrystal body by a scanning transmission electron microscope (STEM).

FIG. 1 illustrates a cross section observation image by a STEM of a polycrystal body represented by a composition deviating from that of the rare earth oxysulfide. A cross section illustrated in FIG. 1 has the polycrystal body 1 represented by the composition deviating from that of the rare earth oxysulfide.

Figure 2:
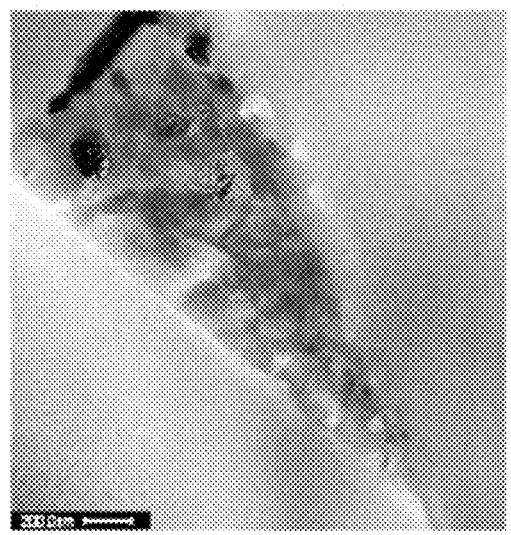
FIG. 2 is a view illustrating an example of an observation image by the STEM of a cross section of a sintered body.
Figure 3:
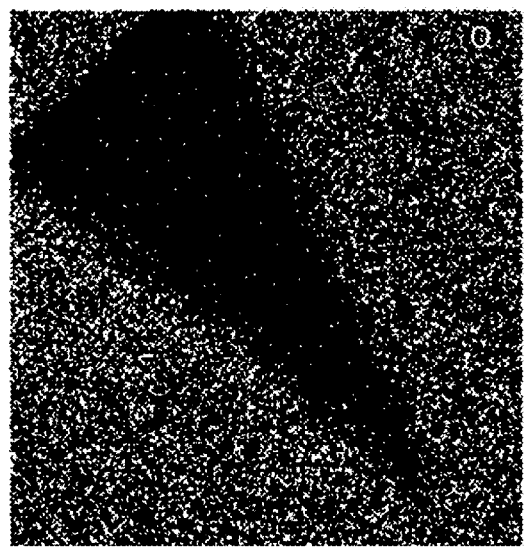
FIG. 3 is a view illustrating an example of a mapping result of oxygen (O) by an energy dispersive X-ray spectroscopy (EDX) of the cross section illustrated in FIG. 2.
Figure 4:
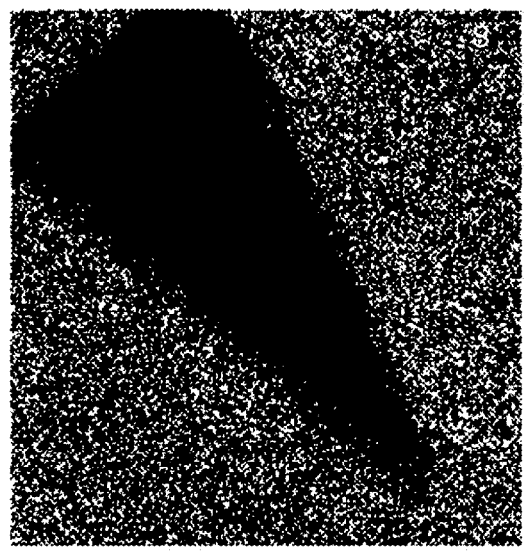
FIG. 4 is a view illustrating an example of a mapping result of sulfur (S) by the EDX of the observation image illustrated in FIG. 2.
Figure 5:
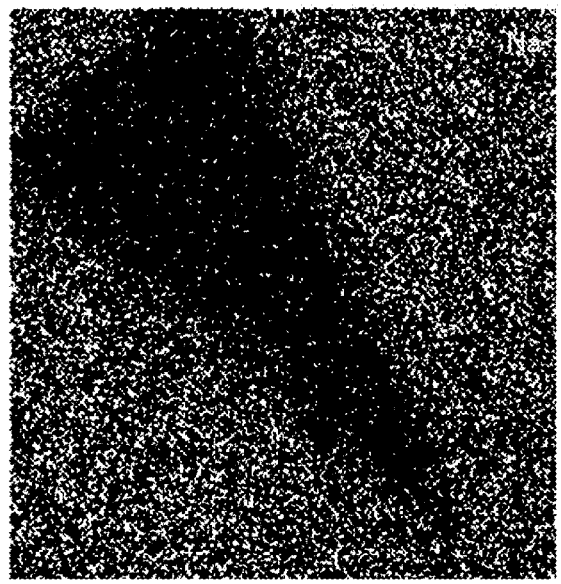
FIG. 5 is a view illustrating an example of a mapping result of sodium (Na) by the EDX of the observation image illustrated in FIG. 2.
Figure 6:
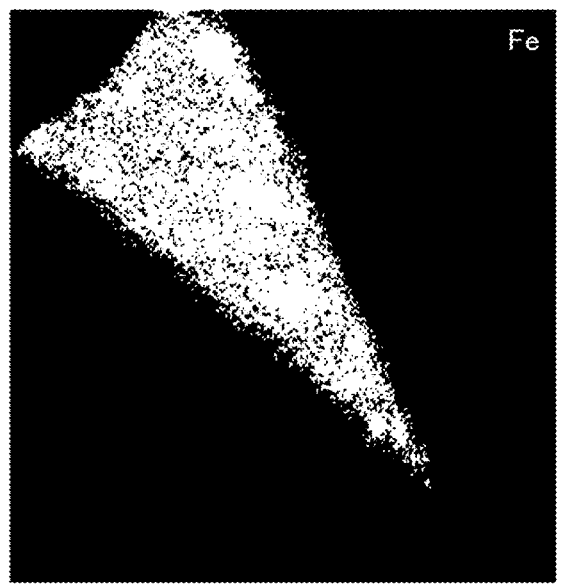
FIG. 6 is a view illustrating an example of a mapping result of iron (Fe) by the EDX of the observation image illustrated in FIG. 2.
Figure 7:
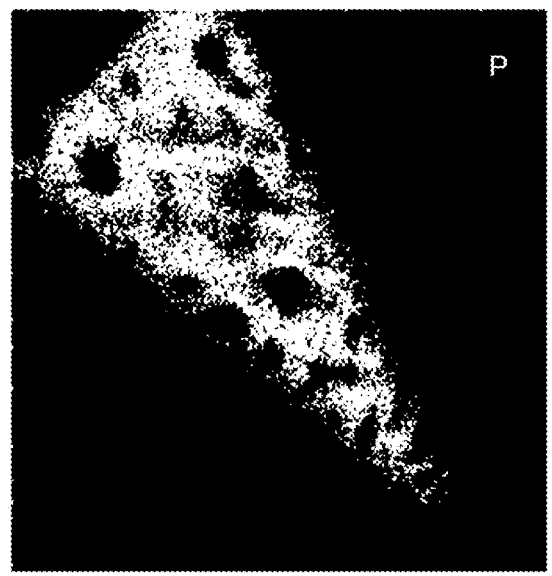
FIG. 7 is a view illustrating an example of a mapping result of phosphorus (P) by the EDX of the observation image illustrated in FIG. 2.
Figure 8:
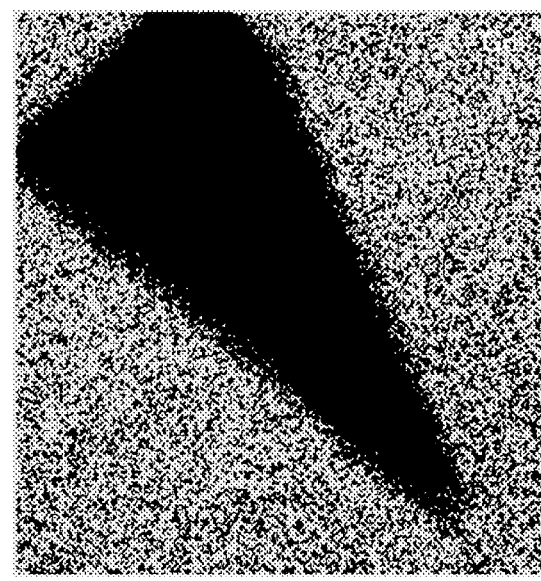
FIG. 8 is a view illustrating an example of a mapping result of gadolinium (Gd) by the EDX of the observation image illustrated in FIG. 2.
Figure 9:
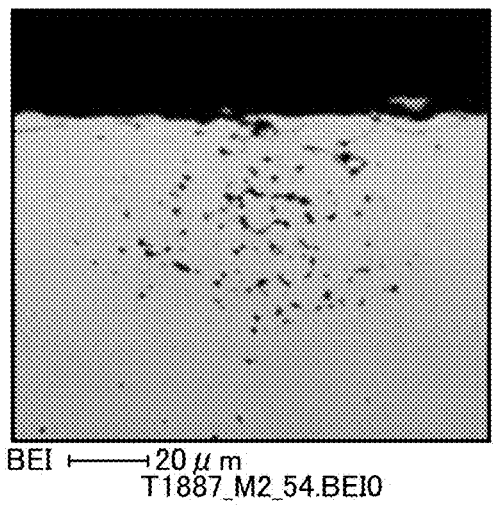
FIG. 9 is a view illustrating an example of an observation image by a scanning electron microscope (SEM) of a cross section of a sintered body.
Figure 10:
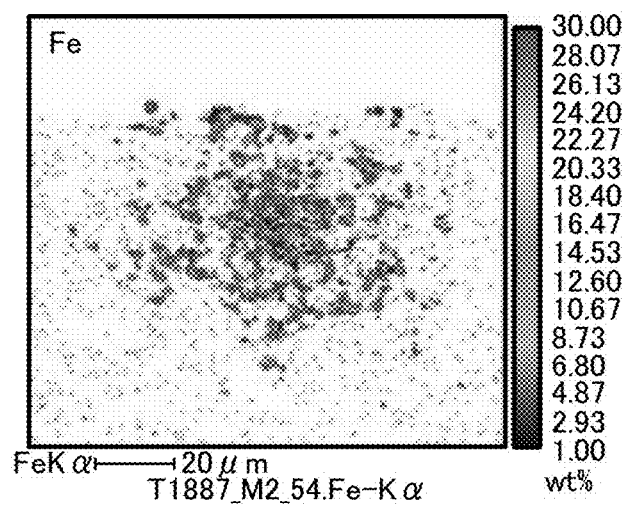
FIG. 10 is a view illustrating an example of a mapping result of iron (Fe) by an electron probe micro analyzer (EPMA) of the observation image illustrated in FIG. 9.
Figure 11:
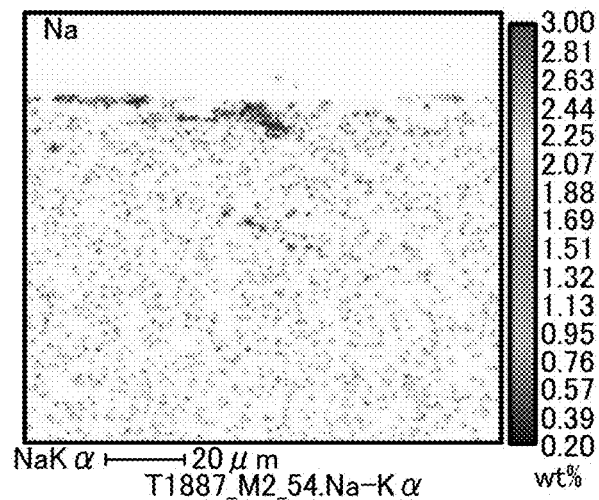
FIG. 11 is a view illustrating an example of a mapping result of sodium (Na) by the EPMA of the observation image illustrated in FIG. 9.
Figure 12:
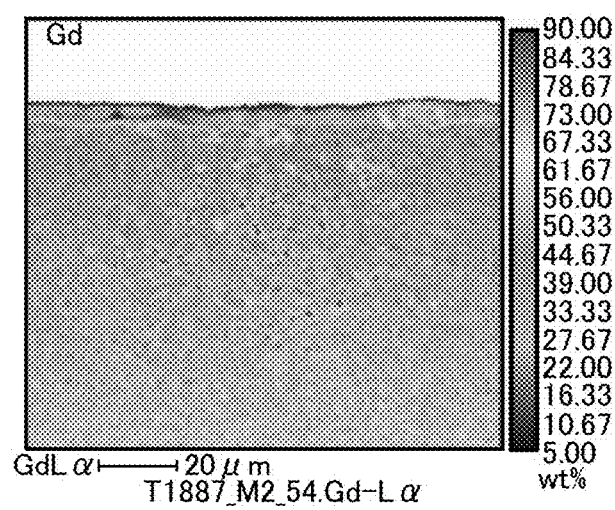
FIG. 12 is a view illustrating an example of a mapping result of gadolinium (Gd) by the EPMA of the observation image illustrated in FIG. 9.
Figure 13:
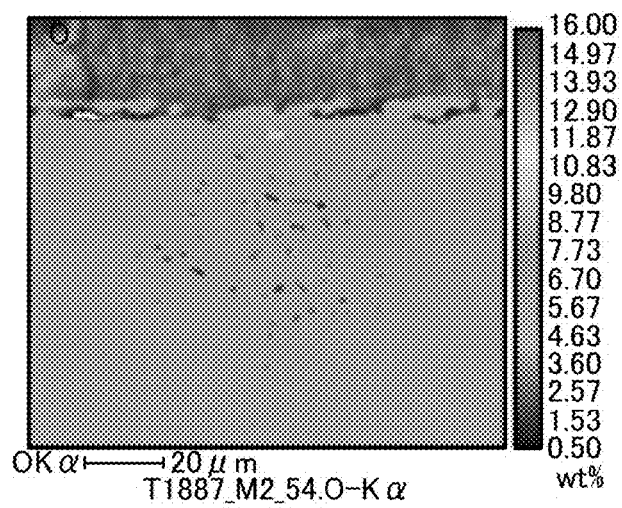
FIG. 13 is a view illustrating an example of a mapping result of oxygen (O) by the EPMA of the observation image illustrated in FIG. 9.
Figure 14:
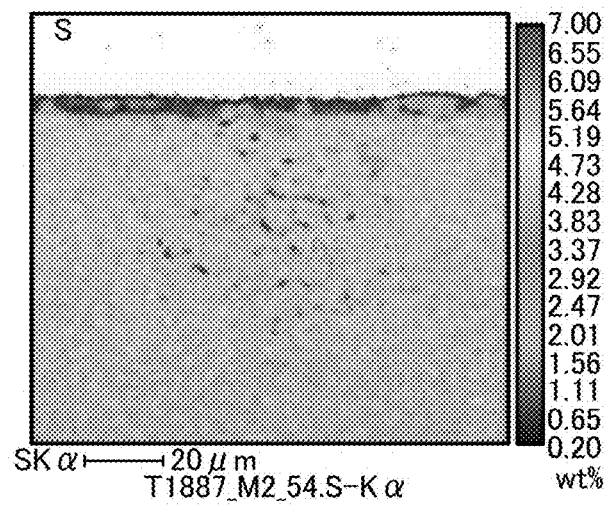
FIG. 14 is a view illustrating an example of a mapping result of sulfur (S) by the EPMA of the observation image illustrated in FIG. 9.
Figure 15:
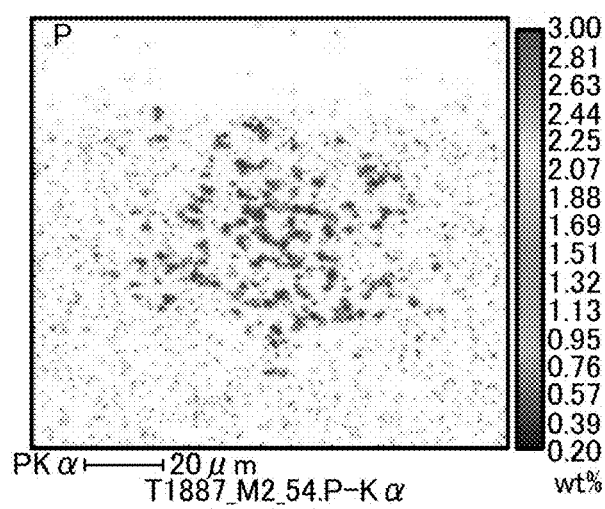
FIG. 15 is a view illustrating an example of a mapping result of phosphorus (P) by the EPMA of the observation image illustrated in FIG. 9.

FIG. 2 is a cross section observation image of a polycrystal body by the STEM, and FIGS. 3 to 8 illustrate examples of mapping results by an EDX of respective elements of the polycrystal body of the observation image illustrated in FIG. 2. FIGS. 3 to 8 reveal that the polycrystal body contains, at a high concentration, impurities such as Fe and P other than Gd, O, and S being original contained elements. FIG. 9 is a cross section observation image by a SEM of a region in which polycrystal bodies gather, while FIGS. 10 to 15 are views illustrating examples of mapping results by the EPMA of respective elements of the region in which the polycrystal bodies gather of the observation image illustrated in FIG. 9. FIGS. 10 to 15 reveal that the region in which the polycrystal bodies gather contains, at a high concentration, impurities such as Fe and P other than Gd, O, and S being the original contained elements.

Examples of the rare earth oxysulfide include a gadolinium oxysulfide ($Gd_2O_2S$), a yttrium oxysulfide ($Y_2O_2S$), and a ruthenium oxysulfide ($Lu_2O_2S$). Further, the rare earth oxysulfide contains at least one element selected from the group consisting of Pr, Ce, Yb, Eu, and Tb as an activator.

The rare earth oxysulfide is preferable to be made of a gadolinium oxysulfide. The gadolinium oxysulfide exhibits a large X-ray absorption coefficient and enables a high optical output. The gadolinium oxysulfide is preferably represented by a composition satisfying a general formula (1) below.

General formula

$$(Gd_{1-a-b}Pr_aM_b)_2O_2S \quad (1)$$

M is at least one element selected from the group consisting of Ce, Yb, Eu, and Tb, a being a number satisfying $0.0001 \leq a \leq 0.01$, b being a number satisfying $0 \leq b \leq 0.005$. The element M is a coactivator and has an effect on controlling an afterglow property or the like. Ce is an element effective in realizing short afterglow. When the gadolinium oxysulfide contains the element M, b is preferably a number satisfying $0.00001 \leq b \leq 0.005$. Part of Gd may be substituted with at least one element selected from the group consisting of Y, La, and Lu.

Figure 16:
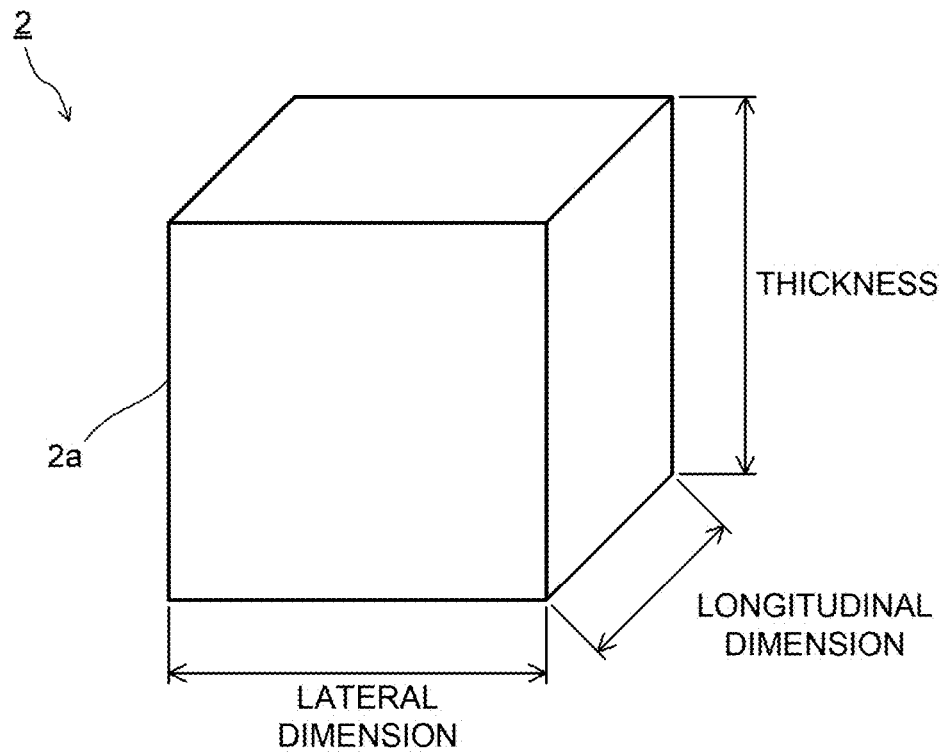
FIG. 16 is a schematic diagram illustrating an example of a scintillator.

FIG. 16 is a schematic diagram exemplifying a ceramic scintillator according to the embodiment. A ceramic scintillator 2 illustrated in FIG. 16 has a sintered body 2a of a regular hexahedron shape or a rectangular parallelepiped shape. A size of the sintered body 2a is not limited in particular as long as being 1 mm³ in volume, and is preferable to be 1 mm or less in longitudinal dimension, lateral dimension, and thickness, respectively. By reducing the minute discoloration region, it is also possible to realize a small-sized ceramic scintillator of 0.8 mm or less in longitudinal dimension, 0.9 mm or less in lateral dimension, and 1.0 mm or less in thickness (ceramic scintillator of 0.72 mm³ or less in volume). Downsizing the ceramic scintillator enables an image detected by an X-ray detector equipped with the scintillator to have higher definition.

The region in which the polycrystal bodies gather is an impurity-containing region which contains at least one selected from the group consisting of a carbonate, iron, aluminum, phosphorus, an alkali metal element, and an alkaline earth metal element.

In an SEM composition image of the ceramic scintillator according to the embodiment, the region in which the polycrystal bodies gather is different in contrast from a crystal region of the rare earth oxysulfide, that is, having a deeper color and being darkly discolored.

At least part of the polycrystal bodies exists in a grain boundary between the rare earth oxysulfide crystal grains. Further, at least part of the polycrystal bodies is likely to exist in a grain boundary triple point among the rare earth oxysulfide crystal grains.

The region in which the polycrystal bodies gather is the impurity-containing region, and examples of the impurity in this region include an impurity contained in a rare earth oxysulfide phosphor powder and an impurity mixed during a manufacturing process. As the major impurity, there can be cited at least one element or a substance selected from the group consisting of a carbonate, iron, aluminum, phosphorous, an alkali metal element, and an alkaline earth metal element. Examples of the alkali metal element, in particular, include Na (sodium) and Li (lithium). Further, examples of the alkaline earth metal element include Ca (calcium). Further, as the impurity metal, there can be cited an element such as Cr (chromium).

As an example of a conventional manufacturing method, there is known a method in which a heat treatment is performed on a rare earth oxysulfide sintered body at 1200 to 1600° C. in an inert gas atmosphere containing oxygen and sulfur to thereby prevent whitening of a sintered body surface and to completely remove internal coloring. The above-described manufacturing method makes it possible to manufacture a sintered body having intended chromaticity coordinates (x, y) by a color meter. Oxygen deficiency and sulfur deficiency can be prevented by such a method.

However, in the above-described manufacturing method, production of a metal oxide and a metal sulfide of the rare earth oxysulfide sintered body is controlled by an oxygen gas and a sulfur gas, and thus, decreasing the metal oxide or the metal sulfide up to the inside of the sintered body is difficult in a case where the rare earth oxysulfide sintered body is large in size. Therefore, when a small ceramic scintillator having a volume of 1 mm³ or less is cut out of a large sintered body (ingot), there is a problem that the metal oxide or the metal sulfide is found remaining only after the scintillator is cut out thereof. Thus, the above-described manufacturing method is poor in mass productivity.

In a case where samples having been cut out to be as small as 1 mm³ or less in volume beforehand is heat-treated in an inert gas atmosphere containing oxygen and sulfur, due to smallness of the respective samples, heat conductivity varies between a lower side and an upper side or between an outer side and an inner side when a large number of samples are put in a baking container. When a heat treatment time is suited to the sample in which heat is not easily conducted, coarse grains are likely to be formed in the sample in which heat is conducted easily. Further, when the heat treatment time is suited to the sample in which heat is conducted easily, an effect on decreasing oxygen deficiency and sulfur deficiency in the sample in which heat is not easily conducted is insufficient. Besides, when the coarse grain is formed, an optical output in a ceramic scintillator having a small volume comes to vary.

The heat treatment in the inert gas atmosphere containing oxygen and sulfur is effective in reducing oxygen deficiency and sulfur deficiency. However, the heat treatment has a small effect on reducing an adverse influence caused by the impurities. Further, when the impurities exist in the rare earth oxysulfide phosphor as oxide or sulfide, a heat treatment for a long period of time is required in order to turn these into oxysulfides completely, and there has been a problem that the heat treatment for a long period of time makes the crystal grain be a coarse grain. In the above-described manufacturing method example, as long as the chromaticity coordinates (x, y) fall within a predetermined range, the scintillator is judged to be a good product, and there has been a portion in which the chromaticity coordinates and reduction in the region in which the polycrystal bodies gather do not necessarily correspond to each other.

Chromaticity confirmation using a color meter has difficulty in detecting the minute oxide region being the region in which the polycrystal bodies gather. A minimum measuring range by a general color meter is about 2 to 8 mm in diameter. With the diameter of 2 to 8 mm or less, a measurement area is 3.14 to 50.24 mm². Even if the minute discoloration region being the region in which the polycrystal bodies gather exists in this range, the range has been recognized as an appropriate range in terms of the chromaticity.

In the sintered body of the scintillator according to the embodiment, even with a small size of 1 mm³ or less in volume, the number of the polycrystal bodies existing in the minute discoloration region being the region in which the polycrystal bodies gather is 200 or less (including zero) per a unit area of 100 µm×100 µm, and an area where the region in which the polycrystal bodies gather exists is 10000 µm² or less (including zero) per a unit area of 500 µm×500 µm.

When the number of the polycrystal bodies existing in the minute discoloration region being the region in which the polycrystal bodies gather is as large as over 200 per the unit area of 100 µm×100 µm, the optical output is reduced. In a small rare earth oxysulfide sintered body having a volume of 1 mm³, the number of the polycrystal bodies existing in the minute discoloration region being the region in which polycrystal bodies represented by a composition deviating from that of the rare earth oxysulfide is preferably 200 or less per the unit area of 100 µM×100 µM The most preferable is a state where the polycrystal body does not exist (the number thereof is zero).

When the area where the region in which the polycrystal bodies gather exists is as large as over 10000 µm² (0.01 mm²) per the unit area of 500 µm×500 µm, the optical output is reduced. Therefore, the area where the region in which the polycrystal bodies gather exists is 10000 µm² (0.01 mm²) or less (including zero) per the unit area of 500 µm×500 µm A sectional structure is observed by using a SEM photograph. The SEM photograph is a composition image with a magnification of 100 times or more. In the composition image, a surface of the region in which the polycrystal bodies gather is different in contrast and shown deeper and darker in color compared with the rare earth oxysulfide region. In the SEM composition image, as an atomic number is larger, a color becomes brighter, and thus Fe (atomic number 26), Na (atomic number 11), Li (atomic number 3), and Ca (atomic number 20), which are impurities, are smaller in atomic number than Gd (atomic number 64), which is a main component, and thus are seen deeper and darker. Therefore, it is easy to distinguish the rare earth oxysulfide region from the impurity-containing region. Further, the EPMA may be used in combination as necessary.

An average crystal grain diameter of the rare earth oxysulfide crystal grains is preferable to be 5 to 30 µm. When the average crystal grain diameter is less than 5 µm, the number of grain boundaries between the rare earth oxysulfide crystal grains increases. Increase in the number of the grain boundaries leads to increase in the number of the regions in which the polycrystal bodies gather which exist in the grain boundary. Meanwhile, when the average crystal grain diameter of the rare earth oxysulfide crystal grains exceeds 30 µm, the grain boundary between the rare earth oxysulfide crystal grains is long. When the grain boundary is long, the region in which the polycrystal bodies gather which exists therein, is likely to be large. Thus, the average crystal grain diameter of the rare earth oxysulfide crystal grains is preferably 5 to 30 µm, and further, more preferably 7 to 20 µm. In order to prevent the grain boundary between the rare earth oxysulfide crystal grains from becoming long, the maximum diameter of the rare earth oxysulfide crystal grains is preferably 50 µm or less. As long as the crystal grain having the maximum diameter of greater than 50 µm exists, even if the average crystal grain diameter is 5 to 30 µm, the grain boundary between the rare earth oxysulfide crystal grains is likely to be long. Therefore, the maximum diameter of the rare earth oxysulfide crystal grains is preferably 50 µm or less, and more preferably 35 µM or less.

The average crystal grain diameter of the rare earth oxysulfide crystal grains is measured by a linear density method. More specifically, a macrophotograph (SEM photograph) of a unit area of 500 µM×500 µm is taken in an arbitrary cross section of the rare earth oxysulfide sintered body. A straight line of 500 µm is drawn by using the macrophotograph. The number of rare earth oxysulfide crystal grains existing on the drawn straight line is counted. An average value is found by (500 µm/number of rare earth oxysulfide crystal grains). The same operation is performed on each of five arbitrary straight lines. An average value of crystal grain diameters of those five straight lines is defined as the average crystal grain diameter.

The scintillator made of the above-described rare earth oxysulfide sintered body, even with a size as small as 1 mm³ or less in volume, exhibits excellent emission characteristics. Further, the ceramic scintillator according to the embodiment is suitable for constituting a ceramic scintillator array by a plurality of the ceramic scintillators being aligned. The ceramic scintillator array is preferable to have the plurality of ceramic scintillators which are integrated via a reflective layer.

Figure 17:
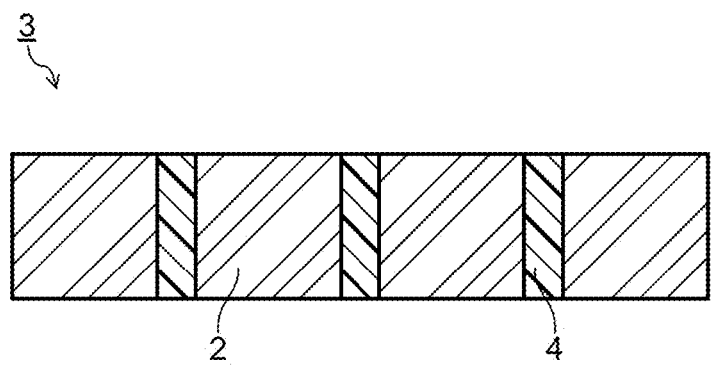
FIG. 17 is a schematic diagram illustrating an example of a scintillator array.
Figure 18:
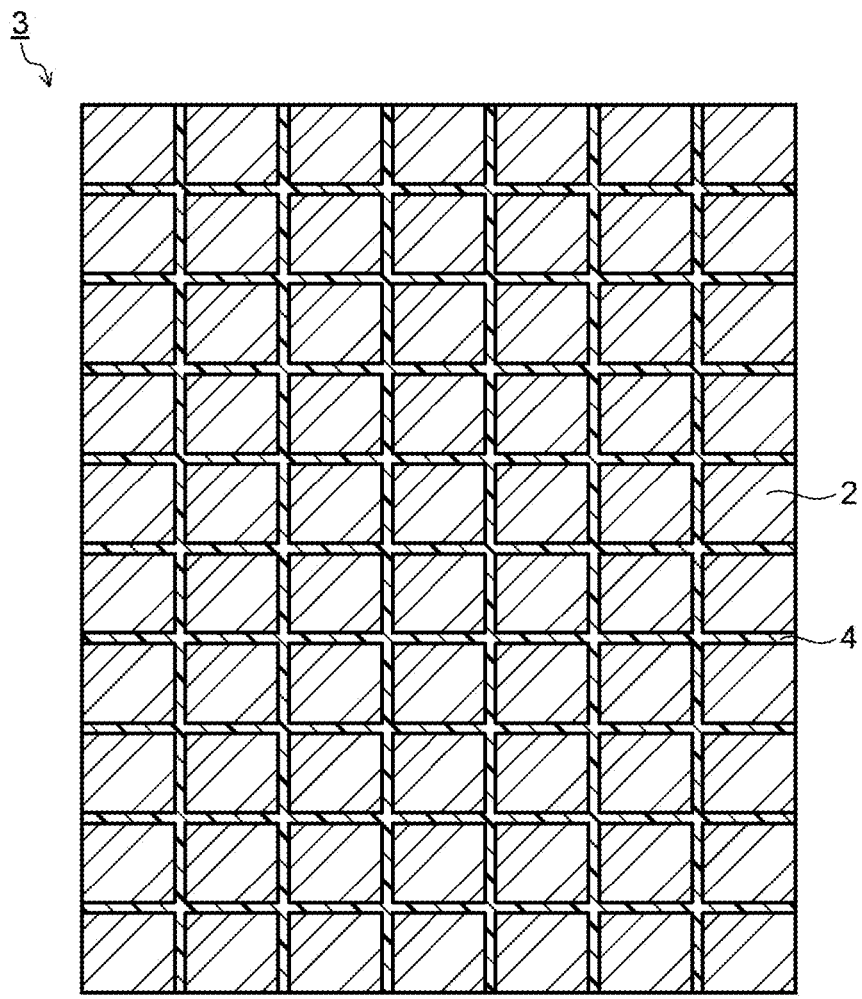
FIG. 18 is a schematic diagram illustrating an example of a scintillator array.

FIG. 17 and FIG. 18 are schematic diagrams exemplifying the scintillator array. FIG. 17 is a side diagram of the ceramic scintillator array, while FIG. 18 is a top diagram of the ceramic scintillator array. A scintillator array 3 illustrated in FIG. 17 and FIG. 18 has ceramic scintillators 2 and reflective layers 4.

The reflective layer 4 is formed of reflective particles of $TiO_2$, $Al_2O_3$, or the like and a transparent resin. The reflective layer 4 may have a structure having a reflective film provided on a side surface of the ceramic scintillator 2 by sputtering or the like. Further, the reflective layer 4 may have a structure in which transparent resins are provided on both surfaces of a metal foil. The reflective layer 4 reflects visible light generated by converting an X-ray incident on the ceramic scintillator 2.

Since the scintillator array according to the embodiment is downsized such that the ceramic scintillator has a volume of 1 mm$^3$ or less, a thickness of the reflective layer (a width between the ceramic scintillators in the reflective layer) can be made as small as 100 μm or less, and further 50 μm or less.

Figure 19:
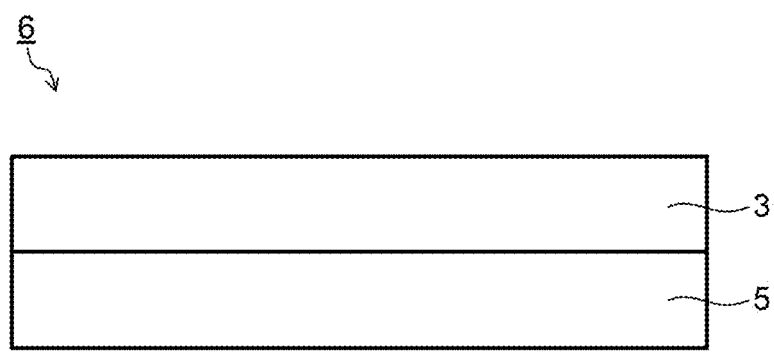
FIG. 19 is a schematic diagram illustrating an example of a radiation detector.

Next, a radiation detector will be described. FIG. 19 is a diagram exemplifying the radiation detector. An X-ray detector 6 illustrated in FIG. 19 has a scintillator array 3 and a photoelectric conversion element 5.

The scintillator array 3 has an X-ray incident surface, and the photoelectric conversion element 5 is integrally provided on a surface on an opposite side to the X-ray incident surface. As the photoelectric conversion element 5, for example, a photodiode is used. The photoelectric conversion element 5 is disposed at a position corresponding to the ceramic scintillator 2 constituting the ceramic scintillator array 3.

The X-ray incident surface of the ceramic scintillator array 3 may be provided with a surface reflective layer. The X-ray detector 6 is constituted by the above. Further, the surface reflective layer may be provided not only on the X-ray incident surface of the scintillator array 3 but may be provided on a mounting surface for the photoelectric conversion element 5. Further, the surface reflective layer may be provided on both the X-ray incident surface and the element mounting surface of the scintillator array 3. Providing the surface reflective layer on the ceramic scintillator array 3 further improves a reflection efficiency of the visible light emitted from the ceramic scintillator 2, and accordingly the optical output of the scintillator array 3 can be increased.

The surface reflective layer contains a mixture of the reflective particles and the transparent resin, a lacquer-based coating material, or the like. The mixture of the reflective particles and the transparent resin preferably has the same dispersion state of the reflective particles as that of the reflective layer 4. A thickness of the surface reflective layer is preferably in a range of 50 to 250 μm. When the thickness of the surface reflective layer is less than 50 μm, a sufficient effect on improving the reflection efficiency cannot be obtained. When the thickness of the surface reflective layer exceeds 250 μm, the X-ray amount transmitted decreases, resulting in a decrease in detection sensitivity.

Figure 20:
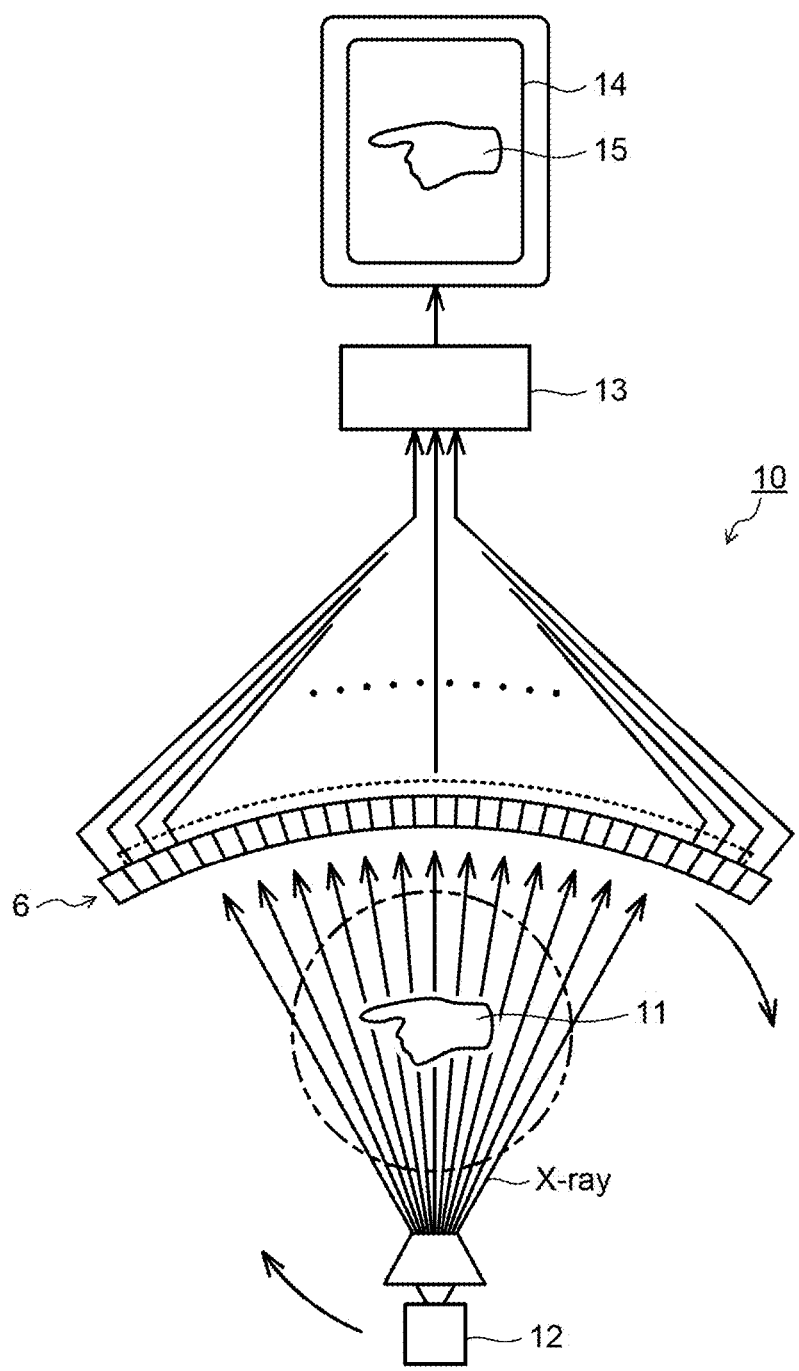
FIG. 20 is a schematic diagram illustrating an example of a radiation inspection device.

Next, a radiation inspection device will be described. FIG. 20 illustrates an X-ray CT scanner 10 being an example of the X-ray inspection device of the embodiment. The X-ray CT scanner 10 includes the X-ray detector 6 of the embodiment. The X-ray detector 6 is pasted on an inner wall surface of a cylinder in which an imaged part of a specimen 11 is put. At an almost center of an arc of the cylinder in which the X-ray detector 6 is pasted, an X-ray tube 12 that emits an X-ray is mounted. Between the X-ray detector 6 and the X-ray tube 12, the specimen 11 is arranged. On the X-ray incident surface side of the X-ray detector 6, a not-illustrated collimator is provided.

The X-ray detector 6 and the X-ray tube 12 are configured to rotate while photographing with the X-ray around the specimen 11. Image information on the specimen 11 is three-dimensionally collected from different angles. Signals obtained by X-ray photography (electric signals converted by the photoelectric conversion element) are processed by a computer 13 and displayed as a specimen image 15 on a display 14. The specimen image 15 is, for example, a tomogram of the specimen 11. Using the scintillator array 3 in which the ceramic scintillators 2 are two-dimensionally arranged as illustrated in FIG. 18 also makes it possible to constitute a multi-tomogram type X-ray CT scanner 10. In this case, a plurality of tomograms of the specimen 11 are photographed at the same time and, for example, a photographing result can be three-dimensionally drawn.

The X-ray CT scanner 10 illustrated in FIG. 20 includes the X-ray detector 6 having the scintillator array 3 of the embodiment. As described above, the scintillator array 3 of the embodiment has an excellent optical output because the reflection efficiency with respect to visible light emitted from the ceramic scintillator 2 is high on the basis of the configuration or the like of the reflective layer 4. Using the X-ray detector 6 having the ceramic scintillator 2 as above makes it possible to shorten a photographing time by the X-ray CT scanner 10. As a result, it is possible to shorten an exposure time of the specimen 11 and achieve reduced exposure. The X-ray inspection device (X-ray CT scanner 10) of the embodiment is applicable not only to X-ray inspection for medical diagnosis of a human body but also to X-ray inspection for animals, X-ray inspection for industrial usage and so on.

The X-ray inspection device according to the embodiment of the present invention enables a high definition image because the scintillator having a volume of 1 mm$^3$ or less is used. Further, the scintillators are each downsized to be 1 mm$^3$ or less in volume and the region in which the polycrystal bodies gather is minimized, resulting in excellent emission characteristics of each of the scintillators. Therefore, the characteristics of the scintillator array in which a plurality of the scintillators according to the embodiment are used are also excellent.

Next, a manufacturing method of the scintillator according to the embodiment will be described. The manufacturing method of the scintillator according to the embodiment is not limited in particular as long as the region in which the polycrystal bodies gather is minimized, but the following can be cited as a method for efficiently obtaining the scintillator. First, a rare earth oxysulfide powder is prepared. The rare earth oxysulfide powder is a phosphor powder. An average grain diameter of the rare earth oxysulfide powder is preferably 10 μm or less, and further preferably 5 μm or less. When the average grain diameter of the rare earth oxysulfide powder is as large as over 10 μm, there is a possibility that a rare earth oxysulfide crystal is too large when made into a rare earth oxysulfide sintered body. When the rare earth oxysulfide crystal is too large, its grain boundary is long. When the grain boundary is long, the region in which the polycrystal bodies gather which exists in the grain boundary is large.

Next, a water-washing process is performed on the rare earth oxysulfide powder. For production of the rare earth oxysulfide powder, flux is used in order to accelerate reaction of the rare earth oxysulfide powder and a sulphidizing agent. The flux is represented by a general formula: $A_3PO_4$, or a general formula: $A_2CO_3$, or the like. An element A is at least one element selected from the group consisting of Li, Na, K, Rb, and Cs. When the flux is used, the element A is likely to remain in the rare earth oxysulfide powder. The element A is a component easily soluble in water as an ion. Therefore, it is effective to perform the water-washing process. Besides, the water-washing process is effective also in removal of impurities mixed inevitably during the manufacturing process. Further, separating impurities in the rare earth oxysulfide powder in the water-washing process, or performing the water-washing process itself in a clean room is also effective in removal of impurities. It is also effective in removal of impurities to let the water-washed rare earth oxysulfide powder pass through a mesh product to thereby remove solid matters therefrom after the water-washing process (screening process).

Next, a process of heat treating the rare earth oxysulfide powder in an inert gas atmosphere containing oxygen and sulfur (first heat treatment) is preferably performed. The heat treatment in the inert gas atmosphere containing oxygen and sulfur makes it possible to reduce the region in which the polycrystal bodies gather in the rare earth oxysulfide powder.

As for the oxygen in the inert gas atmosphere containing oxygen and sulfur, not only an oxygen gas but also the atmosphere or the like can be cited. Further, as for the sulfur, an $SO_X$ gas or the like can be cited. The $SO_X$ gas contains sulfur and oxygen as its constituent, thus making it possible to reduce the region in which the polycrystal bodies gather. As the $SO_X$ gas, an $SO_2$ gas and an $SO_3$ gas can be cited.

A temperature of the heat treatment in the inert gas atmosphere containing oxygen and sulfur is preferably 700 to 1350° C. The heat treatment is intended for the rare earth oxysulfide powder, and thus can be performed at a temperature lower than that of the conventional manufacturing method. A heat treatment time is preferably in a range of 30 minutes to 30 hours. The heat treatment is preferably performed while stirring the inert gas atmosphere containing oxygen and sulfur. Since the heat treatment process is intended for the powder, the atmosphere gas easily comes into contact with each of the rare earth oxysulfide powders as a result that the heat treatment is performed while stirring the atmosphere gas. This leads to reduction in the region in which the polycrystal bodies gather. Further, examples of the method of stirring the atmosphere gas include a method of stirring the atmosphere gas in a heat treatment container, a method of stirring the atmosphere gas while flowing the atmosphere gas, a method of stirring the atmosphere gas while stirring the rare earth oxysulfide powder, and so on.

A rate of increasing a temperature to the heat treatment temperature in the inert gas atmosphere containing oxygen and sulfur is preferably 100° C./min or less. Slow heating at the temperature increasing rate of 100° C./min or less makes it easier for the region in which the polycrystal bodies gather to react with the rare earth oxysulfide. When the temperature increasing rate exceeds 100° C./min, the region in which the polycrystal bodies gather is unlikely to react with the rare earth oxysulfide.

Although the explanation was conducted in the order of the water-washing process and the heat treatment process, a method can be one in which the water-washing process is performed after the heat treatment process, or one in which the water-washing process and the heat treatment process are alternately performed repeatedly. Performing process management as described above enables substantial reduction in the minute discoloration region itself, such as reduction by half.

Next, the rare earth oxysulfide powder is molded. As a molding process, metal mold pressing, rubber pressing, and so on can be cited. Sealing a molded body in a Ta capsule is also effective. In order to remove impurities in the molding process, it is also effective to perform the molding process in a clean room, or to remove impurities attached to employed materials used in the molding process such as a metal mold press, a rubber press, and the Ta capsule before the employed materials are used.

Next, the molded body is sintered. For a sintering process, hot pressing or hot isostatic pressing (HIP) is preferable. Further, in the sintering process it is preferable that a heat treatment temperature is set to 1300 to 1600° C., that a pressure is set to 98 MPa or more, and that a time is set to 1 to 12 hours. Setting such conditions makes it possible to obtain a rare earth oxysulfide sintered body having a relative density of 99.5% or more.

When the heat treatment temperature is as low as less than 1300° C., the sintered body is not densified. Further, when the heat treatment temperature is as high as over 1600° C., the region in which the polycrystal bodies gather is likely to be formed. When the pressure is as low as less than 98 MPa, the sintered body is not densified. In order to reduce the region in which the polycrystal bodies gather, it is preferable not to use a sintering aid. Therefore, the pressure is more preferably 120 MPa or more.

Further, when the sintering time is less than one hour, the sintered body is not densified. When the sintering time exceeds 10 hours, the region in which the polycrystal bodies gather is likely to be formed. Thus, the sintering time is preferably 1 to 12 hours. The sintering time is more preferably 2 to 7 hours.

The second heat treatment in the inert gas atmosphere containing oxygen and sulfur is preferably performed on a sintered body obtained after the sintering process. By this process, the region in which the polycrystal bodies having been formed in the sintering process gather can be reduced. A heat treatment temperature is preferably 700 to 1350° C. A temperature increasing rate of the second heat treatment process is preferably set to 50° C./min or less. Slow heating makes it possible that the region in which the polycrystal bodies gather is generated in the rare earth oxysulfide homogeneously. The temperature increasing rate exceeding 50° C./min cannot realize homogeneous generation. A heat treatment time is preferably in a range of 1 to 40 hours, and further, more preferably in a range of 2 to 20 hours.

As described above, by performing the first heat treatment and the second heat treatment on the rare earth oxysulfide powder, the region in which the polycrystal bodies gather can be reduced. Further, even in a rare earth oxysulfide sintered body ingot of 1 mm or more in longitudinal dimension, 1 mm or more in lateral dimension, and 20 mm or more in length (thickness), it is possible to make the number of the polycrystal bodies existing in the minute discoloration region being the region in which the polycrystal bodies gather be 200 or less (including zero) per the unit area of 100 μm×100 μm and make the area where the region in which the polycrystal bodies gather exists be 1000 μm² or less (including zero). Therefore, it is possible to obtain a ceramic scintillator having a volume of 1 mm³ or less, by cutting out of the rare earth oxysulfide sintered body ingot.

EXAMPLES

Examples 1 to 8, Comparative Examples 1 and 2

Gadolinium oxysulfide powders listed in Table 1 were prepared. As the gadolinium oxysulfide powder, $(Gd_{0.999},$ $Pr_{0.001})_2O_{2\pm0.01}S_{1\pm0.01}$ was used. Next, on the above-described powder, there were performed a water-washing process under a condition listed in Table 1, immersion for a predetermined time period at the time of water-washing, a water-washing process in a clean room, and screening (removal of solid matters) after water-washing. Subsequently, a first heat treatment process (mixed atmosphere of an $SO_2$ gas and the atmosphere) was performed under the condition listed in Table 1, these powders were temporarily molded and then sealed in a Ta capsule to be subjected to a HIP process, and further, a second heat treatment process (mixed atmosphere of an $SO_2$ gas and the atmosphere) was performed, whereby a sintered body was produced. Note that in the water-washing process, washing was performed with pure water.

TABLE 1

| | Presence or Absence of Water-Washing Process | Presence or Absence of Immersion | Presence or Absence of Performing Process in Clean Room | Presence or Absence of Screening | First Heat Treatment Process (Temperature (° C.) × Hour (hr)) | Hip Process (Temperature (° C.) × Hour (Hr)) | Second Heat Treatment Process (Temperature (° C.) × Hour (hr)) |
|---|---|---|---|---|---|---|---|
| Example 1 | Present | Absent | Absent | Absent | 800 × 5 | 1350 × 2 | 900 × 20 |
| Example 2 | Present | Absent | Present | Absent | 1000 × 3 | 1365 × 3 | 1100 × 7 |
| Example 3 | Present | Absent | Absent | Present | 900 × 4 | 1365 × 2 | 1100 × 5 |
| Example 4 | Present | Absent | Present | Present | 1150 × 3 | 1365 × 4.5 | 1200 × 5 |
| Example 5 | Present | Present | Absent | Absent | 1200 × 3 | 1370 × 4.5 | 1200 × 7 |
| Example 6 | Present | Present | Present | Absent | 1100 × 2 | 1365 × 3 | 1150 × 6 |
| Example 7 | Present | Present | Absent | Present | 1100 × 3 | 1365 × 3 | 1200 × 6 |
| Example 8 | Present | Present | Present | Present | 1000 × 2 | 1365 × 3 | 1250 × 6 |
| Comparative Example 1 | Absent | Absent | Absent | Absent | Absent | 1365 × 3 | 1200 × 6 |
| Comparative Example 2 | Absent | Absent | Absent | Absent | Absent | 1365 × 3 | 1150 × 6 |

For each of the ceramic scintillators, there were investigated an average crystal grain diameter of a gadolinium oxysulfide sintered body, the number of polycrystal bodies existing in a minute discoloration region being a region in which the polycrystal bodies gather per a unit area of 100 μm×100 μm, and an area where the region in which the polycrystal bodies gather exists.

In the measurement, an arbitrary cross section of the ceramic scintillator was observed by a SEM. Using a SEM photograph (3000 magnifications), the gadolinium oxysulfide crystal grains shown thereon were found by a linear density method. A straight line of 500 μm being drawn on the SEM photograph, an average value is found by (500 μm/number of rare earth oxysulfide crystal grains). The same operation is performed on each of five arbitrary straight lines. An average value of crystal grain diameters of those five straight lines is defined as the average crystal grain diameter. Further, the longest diagonal line of the gadolinium oxysulfide crystal grains shown on the SEM photograph (3000 magnifications) is searched for and the longest diagonal line is defined as the maximum diameter.

Next, an arbitrary cross section of the ceramic scintillator was analyzed by an EPMA. A measuring spot of the EPMA was set to 100 μm and measurement was performed so that the total becomes a unit area of 100 μm×100 μm. Besides, a composition image of the SEM was observed.

In the ceramic scintillators according to Examples and Comparative examples, at least one element selected from Fe, P, Na, Li, and Ca was detected in minute amounts from the region in which the polycrystal bodies gather. Further, the SEM composition image was photographed, and it was found that the region in which the polycrystal bodies gather is different in contrast and shown deeper and darker in color compared with the rare earth oxysulfide. In the SEM composition image, as an atomic number is larger, a color becomes brighter, and thus Fe (atomic number 26), Na, (atomic number 11), Li (atomic number 3), and Ca (atomic number 20), which are impurities, are smaller in atomic number than Gd (atomic number 64), which is a main component, and thus are seen deeper and darker. Therefore, as the area where the region in which the polycrystal bodies gather exists, an area of a region which is seen different in contrast and shown deeper and darker in color in the SEM composition image was measured.

By the above-described operation, there were found the number of the polycrystal body existing in the minute discoloration region being the region in which the polycrystal bodies represented by a composition deviating from that of the rare earth oxysulfide gather per the unit area of 100 μm×100 μm, and the area where the region in which the polycrystal bodies represented by the composition deviating from that of the rare earth oxysulfide gather exists. Results thereof are listed in Table 2.

TABLE 2

| | Crystal Grain | | Region Containing Polycrystal Body | |
|---|---|---|---|---|
| | Average Crystal Grain Diameter (μm) | Maximum Diameter of Major Axis (μm) | Number of Polycrystal Bodies | AREA (μm²) |
| Example 1 | 8.4 | 12.3 | 127 | 6634 |
| Example 2 | 14.7 | 31.5 | 152 | 6938 |
| Example 3 | 11.3 | 29.3 | 134 | 7203 |
| Example 4 | 19.2 | 37.2 | 116 | 6298 |
| Example 5 | 21.9 | 42.6 | 105 | 5076 |
| Example 6 | 14.5 | 30.7 | 112 | 6165 |
| Example 7 | 15.2 | 39.3 | 103 | 5106 |
| Example 8 | 13.5 | 28.4 | 98 | 4289 |
| Comparative Example 1 | 14.8 | 32.1 | 453 | 26452 |
| Comparative Example 2 | 13.7 | 36.4 | 318 | 17258 |

As is known from Table 2, in each of the ceramic scintillators according to Examples, the area where the region in which the polycrystal bodies represented by the composition deviating from that of the rare earth oxysulfide gather exists is 10000 μm² (0.01 mm²) or less (including zero), and the number was 200 or less (including zero) per the unit area of 100 μm×100 μm.

Next, out of each of sintered body ingots, a sample of 0.7 mm in longitudinal dimension ×0.7 mm in lateral dimension ×0.8 mm in length (thickness) was cut and ceramic scintillators according to Examples and Comparative examples were fabricated. A ceramic scintillator array was fabricated by using the ceramic scintillator according to Example or Comparative example. An epoxy resin containing $TiO_2$ was prepared as a reflective layer. A thickness of the reflective layer was set to 100 μm or 50 μm, and the ceramic scintillators were arranged vertically and horizontally in two dimensions, whereby the ceramic scintillator array was fabricated.

An optical output of the ceramic scintillator array was measured. In the measurement of the optical output, a scintillator array having the same size was fabricated of cadmium tungstate ($CdWO_4$). The scintillator array was set in a radiation detector and a value of electric current to flow through a silicon photodiode when an X-ray having 120 kV and 220 mA was irradiated was found as an optical output. At this time, as a relative value when the optical output of the scintillator array using cadmium tungstate was set to 100, the optical output was found. Results of the above are listed in Table 3.

TABLE 3

| | Relative Value of Optical Output | |
|---|---|---|
| | Reflective Layer Thickness 100 μm | Reflective Layer Thickness 50 μm |
| Example 1 | 207 | 210 |
| Example 2 | 217 | 222 |
| Example 3 | 221 | 227 |
| Example 4 | 226 | 237 |
| Example 5 | 202 | 210 |
| Example 6 | 234 | 237 |
| Example 7 | 213 | 217 |
| Example 8 | 214 | 223 |
| Comparative Example 1 | 189 | 192 |
| Comparative Example 2 | 184 | 187 |

In each of the scintillator arrays according to Examples, the optical output was improved. Since the region in which the polycrystal bodies gather is reduced, excellent characteristics were exhibited even when the width of the reflective layer was set to be as narrow as 100 μm or less, and further 50 μm or less. Therefore, in the scintillator array according to Examples, the reflective layer can be made narrower. In contrast, in Comparative examples, the area of the region in which the polycrystal bodies gather is as large as over 10000 μm$^2$ and the number per the unit area is large, resulting in that improvement of the optical output was not obtained. This reveals that the ceramic scintillator array according to Comparative example is not necessarily appropriate to one in which the thickness of the reflective layer is reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes may be made without departing from the spirit of the inventions. The embodiments and modifications would fall within the scope and spirit of the inventions and fall within the inventions as set forth in accompanying claims and their equivalents. Further, the above-described respective embodiments can be implemented in a manner to be combined mutually.

What is claimed is:

1. A scintillator, comprising;
a sintered body having a volume of 1 mm$^3$ or less, the sintered body including
crystal grains having a crystal region of a rare earth oxysulfide, wherein the rare earth oxysulfide is represented by a general formula $(Gd_{1-a-b}Pr_aM_b)_2O_2S$, wherein M is at least one element selected from the group consisting of Ce, Yb, Eu, and Tb, a is a number satisfying $0.0001 \leq a \leq 0.01$, and b is a number satisfying $0 \leq b \leq 0.005$, wherein an average diameter of the crystal grains is 5 μm or more and 30 μm or less, and wherein a maximum diameter of the crystal grains is 50 μm or less, and
a grain boundary disposed between the crystal grains and having a polycrystal region of polycrystal bodies, wherein each polycrystal body has a different composition from a composition of the rare earth oxysulfide, and wherein each polycrystal body contains iron and phosphorous,
wherein the number of the polycrystal bodies is 200 or less per a unit area of 100 μm×100 μm of a cross section of the sintered body.

2. The scintillator according to claim 1, wherein in an observation image of the cross section by a scanning electron microscope, a contrast of the polycrystal region is different from that of the crystal region, and a color of the polycrystal region is deeper and darker than that of the crystal region, and
wherein an area of the polycrystal region is 10000 μm$^2$ or less per a unit area of 500 μm×500 μm of the cross section.

3. The scintillator according to claim 1, wherein each polycrystal body further contains at least one element selected from the group consisting of a carbonate, iron, aluminum, phosphorous, an alkali metal element, and an alkaline earth metal element.

4. A scintillator array comprising:
a first scintillator;
a second scintillator; and
a reflective layer between the first and second scintillators,
wherein each of the first and second scintillators is the scintillator according to claim 1.

5. The scintillator array according to claim 4, wherein the reflective layer contains a titanium oxide or an aluminum oxide.

6. The scintillator array according to claim 4, wherein a width between the first and second scintillators in the reflective layer is 100 μm or less.

7. A radiation detector comprising the scintillator array according to claim 4.

8. A radiation inspection device comprising the radiation detector according to claim 7.

9. A scintillator, comprising:
a sintered body having a volume of 1 mm$^3$ or less, the sintered body including
crystal grains having a crystal region of a rare earth oxysulfide, wherein the rare earth oxysulfide is represented by a general formula $((Gd_{1-\alpha}X_\alpha)_{1-a-b}Pr_aM_b)_2O_2S$, wherein X is at least one element selected from the group consisting of Y, La, and Lu, M is at least one element selected from the group consisting of Ce, Yb, Eu, and Tb, $\alpha$ is a number satisfying $0 < \alpha < 1$, a is a number satisfying $0.0001 \leq a \leq 0.01$, and b is a number satisfying $0 \leq b \leq 0.005$, wherein an average diameter of the crystal grains is 5 μm or more and 30 μm or less, and wherein a maximum diameter of the crystal grains is 50 μm or less, and a grain boundary disposed between the crystal grains and having a polycrystal region of polycrystal bodies, wherein each polycrystal body has a different composition from a composition of the rare earth oxysulfide, and wherein each polycrystal body contains iron and phosphorous, wherein the number of the polycrystal bodies is 200 or less per a unit area of 100 μm×100 μm of a cross section of the sintered body.

* * * * *